(12) United States Patent
Yoneda et al.

(10) Patent No.: US 7,643,746 B2
(45) Date of Patent: Jan. 5, 2010

(54) LIGHT INTENSITY ADJUSTING SYSTEM

(75) Inventors: Kenji Yoneda, Kyoto (JP); Shigehide Hirooka, Kyoto (JP)

(73) Assignee: CCS Inc., Kyoto (JP)

( * ) Notice: Subject to any disclaimer, the term of this patent is extended or adjusted under 35 U.S.C. 154(b) by 1050 days.

(21) Appl. No.: 10/534,613

(22) PCT Filed: Nov. 14, 2003

(86) PCT No.: PCT/JP03/14552

§ 371 (c)(1),
(2), (4) Date: May 11, 2005

(87) PCT Pub. No.: WO2004/044565

PCT Pub. Date: May 27, 2004

(65) Prior Publication Data

US 2006/0050499 A1 Mar. 9, 2006

(30) Foreign Application Priority Data

Nov. 14, 2002 (JP) ............................. 2002-331413

(51) Int. Cl.
*G03B 9/70* (2006.01)
*G03B 15/03* (2006.01)

(52) U.S. Cl. ...................................... 396/182; 396/164

(58) Field of Classification Search ................. 396/155, 396/164, 182; 348/370; 362/11
See application file for complete search history.

(56) References Cited

U.S. PATENT DOCUMENTS

| 4,315,245 | A | | 2/1982 | Nakahara et al. |
| 5,466,922 | A | | 11/1995 | Gatto et al. |
| 6,101,749 | A | * | 8/2000 | Inbar et al. ..................... 40/361 |
| 6,359,662 | B1 | * | 3/2002 | Walker ........................ 348/743 |
| 2003/0215129 | A1 | * | 11/2003 | Yang et al. .................. 382/149 |

FOREIGN PATENT DOCUMENTS

| DE | 100 17 380 | 11/2000 |
| GB | 2 350 423 | 11/2000 |
| JP | 62-166478 | 7/1987 |
| JP | 63-184171 | 7/1988 |
| JP | 01-297534 | 11/1989 |
| JP | 04-248449 | 9/1992 |
| JP | 10-111251 | 4/1998 |

* cited by examiner

*Primary Examiner*—Rodney E Fuller

(57) ABSTRACT

A light intensity adjustment system is provided which greatly decreases or makes unnecessary image compensation by the image processing device side, improves scan precision, and can reduce the scan time; and which comprises: a light irradiation device 1 that has multiple independently light intensity adjustable light irradiation units 11, and that irradiates light facing a predetermined target area A; a photographic device 2 that photographs said target area A through a lens, and outputs a target area image that is the photographed image; and a light intensity control unit 3 that controls the respective light intensities of said light irradiation units 11 so that the brightness of the various parts of the target area images that said photographic device 2 has output approaches a predetermined standard value.

14 Claims, 20 Drawing Sheets

EXAMPLE OF INDIVIDUAL LIGHT IRRADIATION ASPECT DATA (TABLE)

| LIGHT IRRADIATION UNIT IDENTIFIER | CENTRAL POSITION | IRRADIATION RANGE |
|---|---|---|
| A | 20 | 10~30 |

| POSITION / CURRENT | 00 | 01 | 02 | 09 | 10 | 11 | 19 | 20 | 21 | 29 | 30 | 31 | 98 | 99 |
|---|---|---|---|---|---|---|---|---|---|---|---|---|---|---|
| 001 | 00 | 00 | 00 | 01 | 01 | 01 | 03 | 03 | 03 | 01 | 01 | 01 | 00 | 00 |
| 002 | 00 | 00 | 00 | 01 | 01 | 01 | 03 | 03 | 03 | 01 | 01 | 01 | 00 | 00 |
| ⋮ | ⋮ | ⋮ | ⋮ | ⋮ | ⋮ | ⋮ | ⋮ | ⋮ | ⋮ | ⋮ | ⋮ | ⋮ | ⋮ | ⋮ |
| 249 | 00 | 00 | 00 | 01 | 03 | 06 | 260 | 262 | 260 | 07 | 03 | 01 | 00 | 00 |
| 250 | 00 | 00 | 00 | 01 | 03 | 07 | 261 | 263 | 261 | 08 | 04 | 01 | 00 | 00 |

BRIGHTNESS

FIG.16

LIGHT INTENSITY ADJUSTING SYSTEM

TECHNICAL FIELD

The present invention is related to a light intensity adjustment system for adjusting the light intensity to irradiate when conducting external appearance scans and defect scans by photographing the target area of a work piece.

BACKGROUND ART

In the past, when conducting inline high-speed scans of WEB (continuous objects: film, paper, sheet metal) and BATCH (sheet products, individual products: cut film, cut glass, drums), which are the objects to be scanned, scans for surface defects were conducted by using line sensor cameras, incorporating the surface of the flowing work pieces as continuous image data, and, with an image data processor, detecting areas that differ in brightness.

At that time, in order to precisely detect surface faults, it was necessary to illuminate uniformly with a fixed illumination intensity the area targeted for photography by said camera, and conventionally halogen lamps and fluorescent lights were used as the light irradiation devices for this purpose. Moreover, devices using LEDs that are superior in velocity responsiveness, stability of light intensity, and lifetime, etc. have recently been developed as a substitute for these light sources.

In this regard, even though illumined uniformly without unevenness on the area targeted for photography, the brightness level of the photographed image is higher in the central part and increasingly lower toward the edges because of lens aberration (distortion), or differences in the distance between the camera and the parts of the area targeted for photography or differences of image angle. In particular, this tendency is notable if using a wide-angle lens. Concretely, indicated in FIG. 15 is a depiction of video signals (signals of light received by a camera (CCD) converted to electronic signals), which are output from a camera.

Thus, in the past, after incorporating the image signals from the camera, the brightness of these signals was adjusted (shading compensation) on the image processor side by compensating on the signal level, for example, digitally, and scan processing was conducted thereafter. Typically, there are addition and subtraction devices that add brightness that is lacking to dark areas of the incorporated image that should have a fixed level of brightness, and subtract brightness from parts that are too bright; and there are devices that compensate the brightness of the various parts to a fixed level by gain control (multiplication). Further, there are a variety of methods that form the basis of compensation in these methods, as represented by Patent Literature (Japanese Unexamined Patent Application Publication No. H10-111251).

Nonetheless, when conducting shading compensation on the image processor side, there is the risk that image deterioration when converting the digital signals and differences in the calculation method during compensation may have a deleterious effect on the precision of detecting defects, etc. This will be explained by citing specific examples.

As indicated in FIG. 24, for example, the central part and the edge part in the width direction respectively have the same defect. Nonetheless, the brightness level that is entered as a signal for the defect at the edge is smaller because of the darkness.

When, for example, shading compensation is conducted from the image processor side with said addition and subtraction making the brightness levels of the whole uniform, as indicated in FIG. 25, a difference in those brightness levels may be generated because only the background is compensated and no changes are generated in the relative level of the defect from the background, irrespective of the central part and the edge having the same defect, and thus there is the specific risk of variance in the detection of defects. For example, if the threshold level of defect detection were set at the dotted line in this diagram, the defect on the edge would not be detected.

Meanwhile, if shading compensation is conducted from the image processor side with said gain control (multiplication) making the brightness levels of the whole uniform, as indicated in FIG. 26, the defect levels of the central part and the edge are uniform because both the background and the defect levels are compensated. However, gain control also amplifies noise near the edge, and produces the risk of mistakenly detecting this noise as a defect. For example, if the threshold level of defect detection were set at the dotted line in this diagram, the noise would be detected as a defect.

Further, because the load on the image processing side becomes larger, there is a resulting disadvantage that the scan time cannot be shortened without shortening the image processing time; and there is also the disadvantage that costs will increase if the scale of the image processor is increased. Moreover, there are devices that conduct the same kind of shading compensation on the photographic equipment side, but the same kinds of image deterioration, etc. can occur.

DISCLOSURE OF THE INVENTION

Thus, the present invention is a device that attempts to change the approach and control the light irradiation device such that, when the camera incorporates the image, for example, the brightness of the target area of that image is made uniform, or unevenness is positively generated; and by greatly reducing or making unnecessary the image compensation processing by the image processor side, addresses the problems of interest, namely, to improve scan precision by preventing false detection that can be generated when conducting compensation processing on that image; and to shorten scan time.

Specifically, the present invention is a light intensity adjustment system that comprises: a light irradiation device that provides multiple light irradiation units that are independently light intensity adjustable, and that irradiate light toward predetermined target areas; a photographic device that photographs said target areas through a lens, and outputs target area images that are the photographed images; and a light intensity control unit that controls the respective light intensities of said light irradiation units so that the brightness of the various parts of the target area images that said photographic device has output approaches a predetermined standard value.

More concretely, the present invention comprises: a light irradiation device that irradiates light on a predetermined target area set up on a work piece; and a photographic device that photographs that target area, and outputs the obtained target area images to an image processor for the purpose of a surface scan; characterized in that: said light irradiation device has multiple light irradiation units that are independently light intensity adjustable; and a light intensity control unit is further provided to control the respective light intensities of said light irradiation units so that the brightness of the various parts of the target area images that said photographic device has output approaches a predetermined standard value.

With this kind of device it is possible to prevent diminishing scan precision caused by image deterioration when compensating because it is possible to greatly reduce or make unnecessary image compensation processing, such as shading compensation by the image processor side. In addition is becomes possible to broadly promote shortening scan time and improving scan precision because the image processing device can concentrate on the original image processing necessary for scanning.

Here, the various light irradiation units may be light emitting bodies such as one or multiple LEDs, etc., or the light exit end of a light guide such as optical fibers. If using a light guide, separate light emitting bodies are necessary.

When using to scan for defects, it is preferable to control the light intensities of the various light irradiation parts oriented toward making the brightness of the various parts of said target area images uniform.

Slight differences in the respective light intensities and irradiation angles caused by fluctuations of product quality and mounting errors, etc. can occur in the light irradiation units. In relation to this, there is the risk that the device may become inadequate from the perspective of control speed and control error, etc. because each irradiation unit is controlled in the same way. To suitably resolve this problem, it is preferable to further comprise an individual light irradiation aspect data memory unit, whereby light irradiation aspects on said target area based on the light irradiated from the individual light irradiation units are acquired in advance from said target area images and are memorized as individual light irradiation aspect data; and to provide a configuration that controls the light intensities of said light irradiation units based on said individual light irradiation aspect data.

Data that at least indicates the light irradiation range and brightness distribution on the target area by the various light irradiation units that are supplied a predetermined power may be cited as concrete contents of said individual light irradiation aspect data.

Attempting to simplify control, it is preferable to divide said target area into multiple unit areas, to make one light irradiation unit mainly irradiate a unit area corresponding to the unit area in question, and to make that light irradiation unit be the main light irradiation unit of the unit area in question. In this way if only the main light irradiation unit controls the brightness of one unit area, light intensity control is simplified.

Concretely, it is preferable that there be a one to one correspondence between said unit areas and the light irradiation units.

Dividing said target area into multiple unit areas so that the number or type of light irradiation units that irradiate the unit areas with light respectively differ based on the range of light irradiation of the various light irradiation units indicated by said individual light irradiation aspect data may be cited as a method of division into unit areas. Moreover, in this case, the light irradiation unit that gives the most light intensity to the various unit areas may be taken as the main light irradiation unit of the unit area in question based on the brightness distribution of the various light irradiation units indicated by said individual light irradiation aspect data.

A preferable concrete form of realizing this may include a device wherein said light intensity control unit comprises: an image separation unit that separates said target area image into images of said unit areas; a representative value calculation unit that calculates the representative value of the brightness of the unit area images; a comparison unit that compares the representative values of said unit area images with a predetermined standard value of the brightness; and a unit light intensity control unit that controls the light intensity of the main light irradiation unit corresponding to the unit area in question, such that the various representative values approach said standard value based on the results of comparisons by said comparison unit.

The mean brightness of the unit area image is preferable as the representative value in this case.

If the scan object is a WEB, then a light irradiation device that lines up the light irradiation units in a linear shape is preferable, but when a BATCH, a light irradiation device that lines up the irradiation units in the surface shape is acceptable. Here, the meaning of surface is not limited to planar, and also includes curved surfaces.

Preferably, the light irradiation device comprises a light intensity unevenness-mitigating member that mitigates light intensity unevenness dependent on the gaps between adjacent light irradiation units. In line illumination, a lenticular lens that diffuses the light only in a fixed direction may be cited as this light intensity unevenness-mitigating member, and in surface illumination, a light diffusion plate may be cited.

Moreover, if multiple photographic devices are comprised and said target area is photographed by dividing said target area based on these photographic devices, overlapping photographs of a part of said target area by adjacent photographic devices may occur. In this case, there is the problem of which image of the overlapping area obtained from the photographic devices is to form the basis for controlling the light intensity. In this case, for overlapping target areas, it is preferable to control the light intensity of the corresponding light irradiation unit based on the image obtained by the photographic device with the higher priority ranking, and for the target area that the photographic device with the lower priority ranking photographs, the light intensity of the light irradiation unit corresponding to the other area is controlled taking the image of the previously described overlapping area as a standard.

BRIEF DESCRIPTION OF THE DRAWINGS

FIG. 16 is a frame format data structure diagram indicating the structure of the individual light irradiation aspect data of the same embodiment.

BEST MODE FOR CARRYING OUT THE INVENTION

An embodiment of the present invention will be explained below by referring to the diagrams.

First Embodiment

Figure 1:
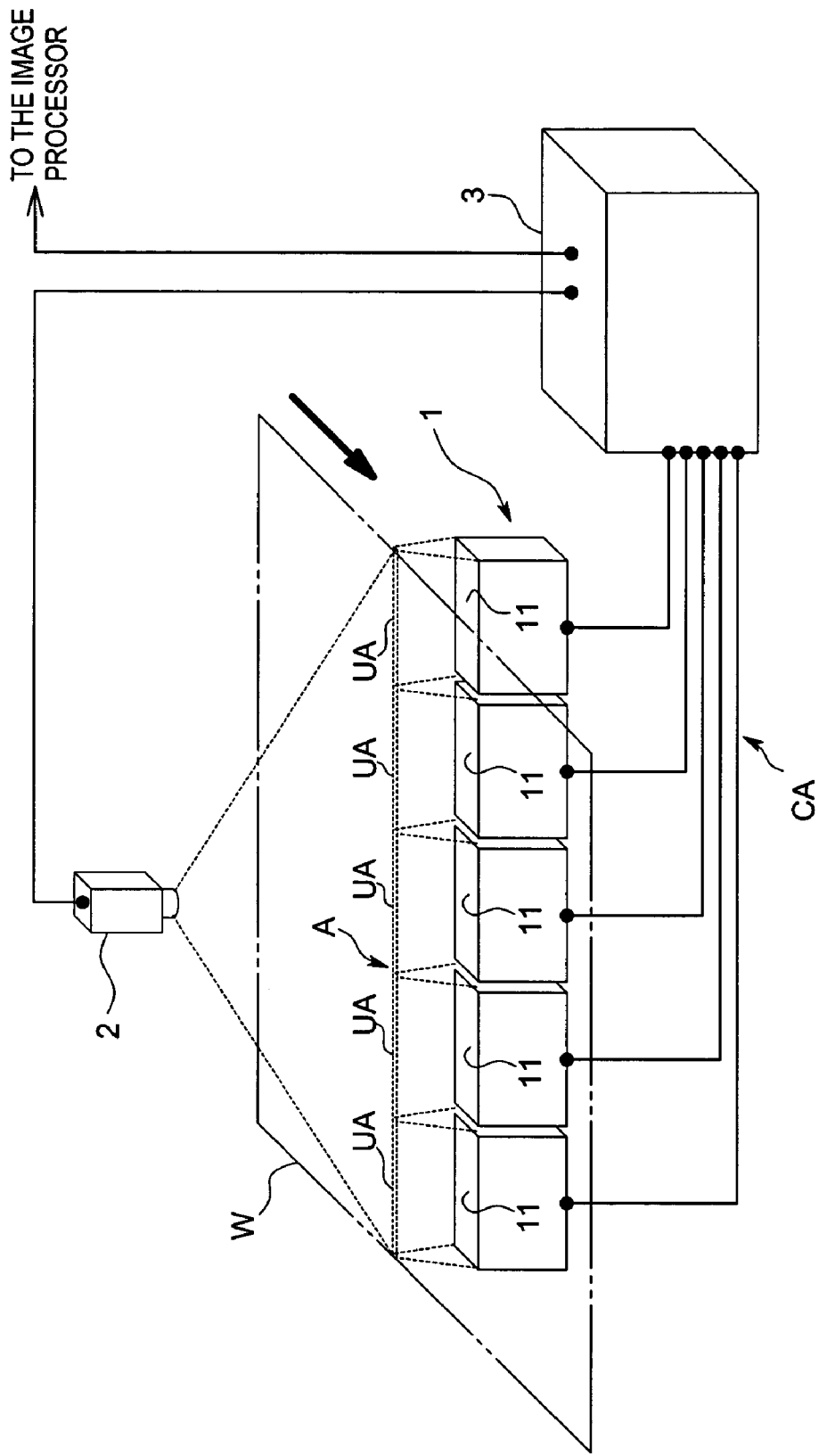
FIG. 1 is an overall conceptual configuration diagram of a light intensity adjustment system of the first embodiment of the present invention.

FIG. 1 indicates an overall summary of a light intensity control system related to the present embodiment. This light intensity control system is, for example, used in a surface scan of a product, etc.; the scan object (work piece) W of the present invention is, for example, a continuous object such as translucent paper or film; and is set up to flow in a predetermined direction at a fixed speed.

Accordingly, as indicated in the same diagram, this light intensity control system comprises: a light irradiation device 1 that has multiple independently light intensity adjustable light irradiation units 11, and irradiates light toward the back surface predetermined region of said work piece W; a photographic device 2 that photographs the light irradiated predetermined target area A from the front surface through a lens not indicated in the diagram, and outputs target area images, which are the photographed images; and a light intensity control unit 3 that controls the respective light intensities of said light irradiation units 11 so that the brightness of the various parts of the target area images that said photographic device 2 outputs approach a standard value.

The various parts will be described in detail.

Figure 2:
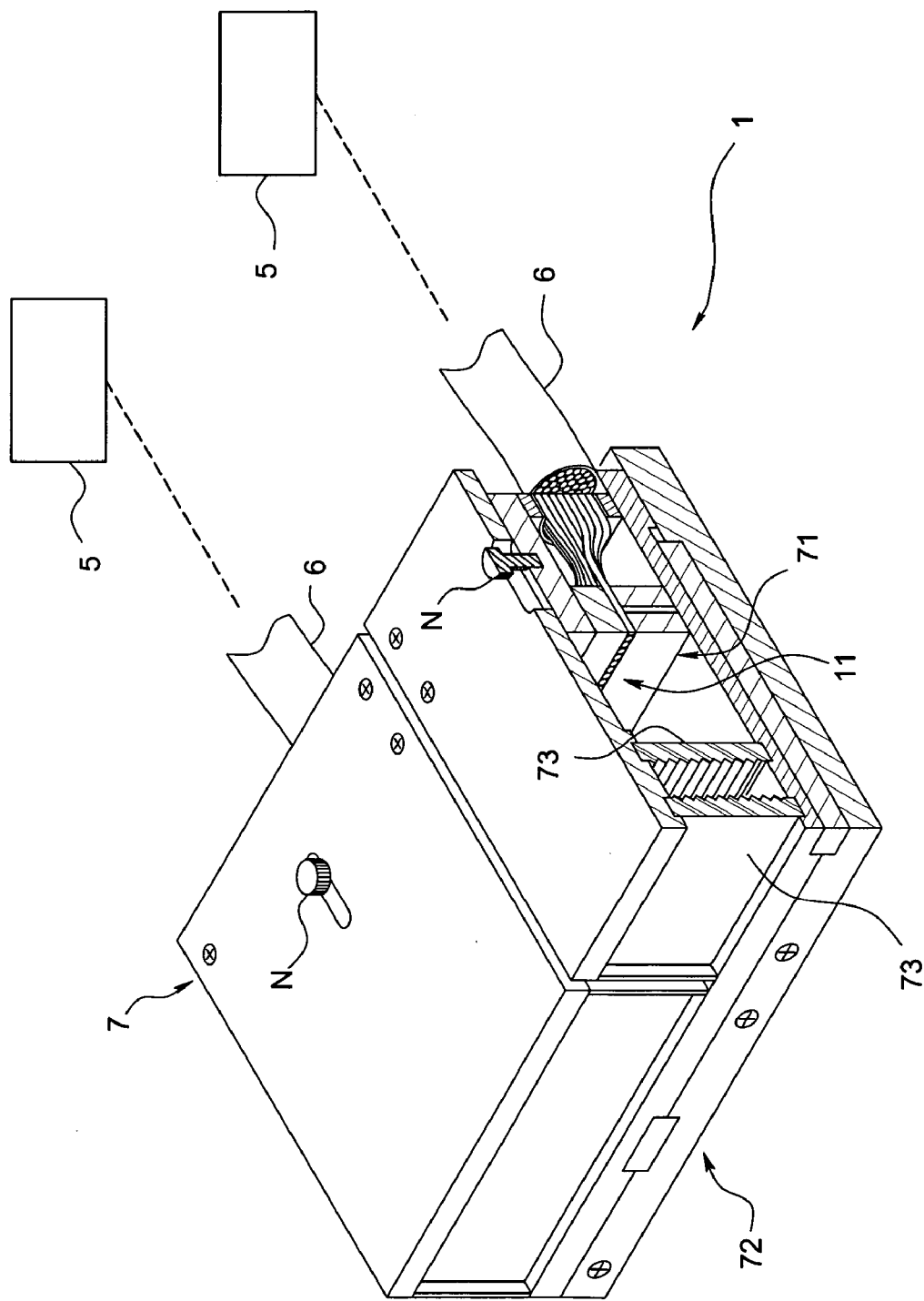
FIG. 2 is a partial cut-away perspective view diagram of a light irradiation device of the same embodiment.
Figure 3:
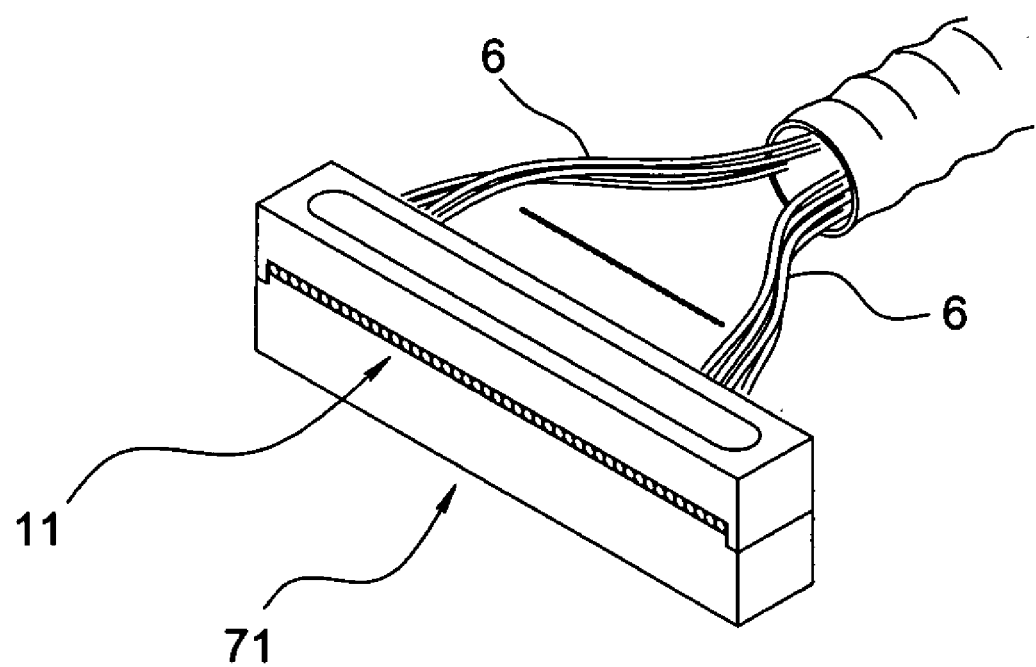
FIG. 3 is an perspective view diagram indicating a holder of the same embodiment.

As indicated in FIG. 2 and FIG. 3, the light irradiation device 1 comprises: multiple power LEDs 5 that are light emitting bodies; optical fibers 6 that are flexible light guides that lead the light exiting from the various power LEDs 5; and a casing 7 that supports the light exiting end of the optical fibers 6.

The multiple optical fibers 6 are respectively connected to the power LEDs 5, and said casing 7 comprises multiple holders 71 that support the light exiting end of a group of optical fibers 6 connected to these power LEDs 5, and a casing main body 72 that supports these holders 71 in a row to be orthogonal to the direction of flow of said work piece W. The light exiting ends of said group of optical fibers 6 are supported in a line and in the same direction by one holder 71, and configure one light irradiation unit 11 having a linear shape. Further, the optical fibers 6 are pinched in the holder 71, and, for example, are fixed with an adhesive.

Then, the light emitted from the various light irradiation units 11 irradiate at a nearly one to one correspondence in multiple unit areas UA, into which said target area A is divided, and as a whole makes a continuous line of illumination of a predetermined width. Moreover, a pair of refractive lenses 73 (Fresnel lenses), which refract the linear shaped light exiting from said light irradiation units 11 so that the width is narrowed, are mounted in said casing 7. The holder 71 is configured to be position changeable in relation to the casing main body 72 by loosening and tightening a screw N. By modifying the distance between the light irradiation units 11 and the lens 73, the angle at which the exiting light is brought together can be changed. Further, the power LEDs 5 are ultra-high brightness LEDs, each of which has a current of approximately 200 mA when connected in a single unit.

Figure 4:
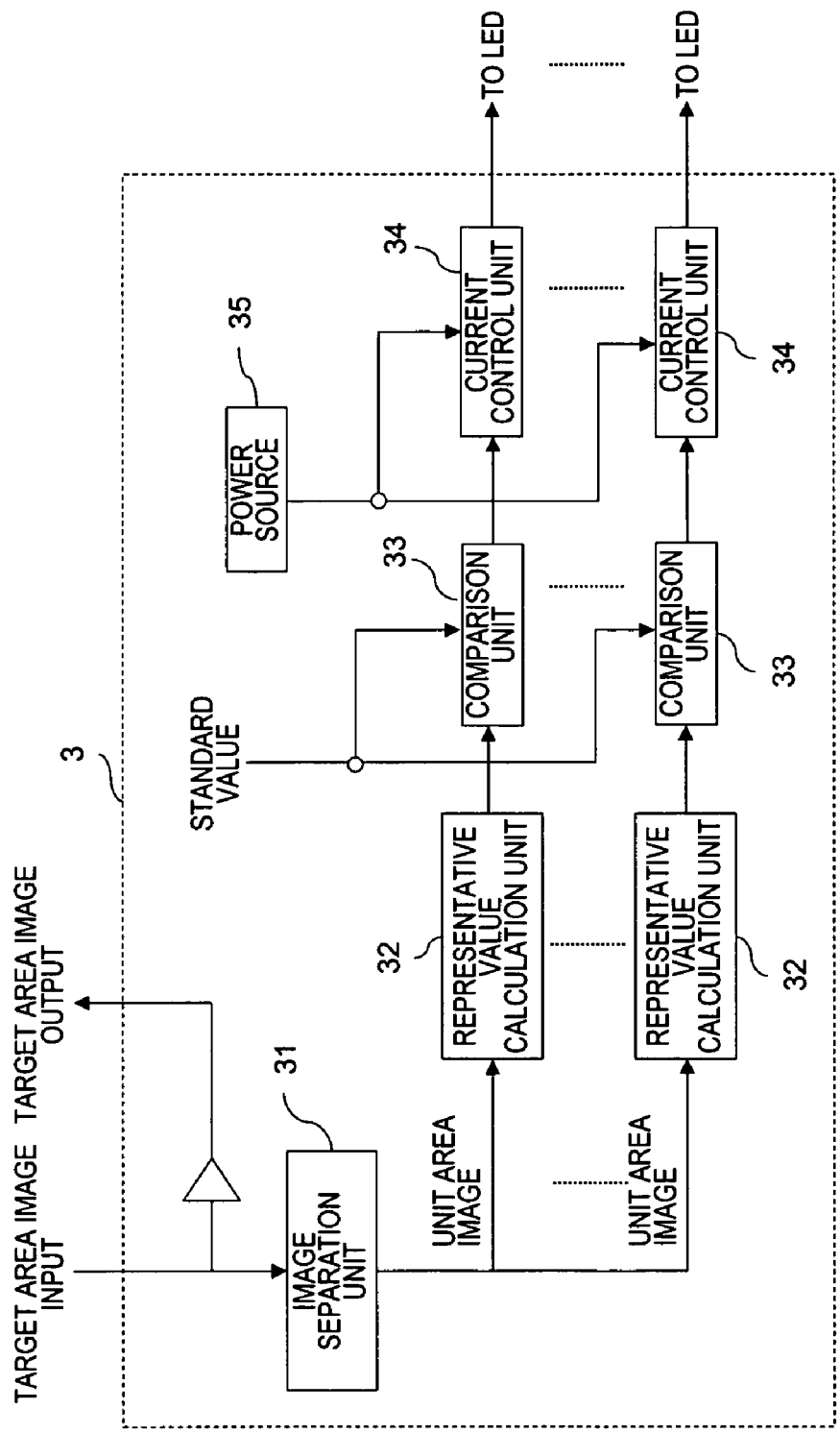
FIG. 4 is a functional block diagram of the light intensity control unit of the same embodiment.

The photographic device 2 is, for example, called a line sensor camera, and has CCD elements lined up in one row. Then, the light exiting from said predetermined region is focused on the light receiving surfaces of these CCD elements through, for example, a wide angle lens, not indicated in the drawing, provided in this photographic device 2; this incident light is converted to electric signals, and is output as image signals that can be processed as an image. As indicated in FIG. 4, these image signals are transmitted to an image processing device for surface scanning, and in parallel with this, the image signals are also transmitted to the light intensity control unit 3 that will be described later.

The light intensity control unit 3 is connected to the various power LEDs 5 through a current cable CA, and controls the current provided to these, and also serves as the power source of the light irradiation device 1. This light intensity control unit 3 is a separate unit from said light irradiation device 1, and as indicated in the functional block diagram in FIG. 4, comprises: a power source 35; an image separation unit 31 that separates said image signals into unit area image signals for every unit area UA; representative value calculation units 32 that calculate from these signals the representative value of the brightness (luminance level) of the various unit area images; comparison units 33 that compare the representative values of the various unit area images with a predetermined standard value of brightness; and current control units 34 that are unit light intensity control unit to control the supply current to the corresponding power LEDs 5 such that the various representative values approach said standard value based on the results of comparisons by said comparison units 33. The functions as these units are manifested by operating a CPU or its peripheral devices in accordance with a program memorized in memory not indicated in the diagram, or by operating a discrete circuit such as an analogue amplifier, etc. Further, in this embodiment, said representative value is the average value of the brightness of said unit area images. This is because the signal strengths may be simply integrated.

One example of the operation of a light intensity adjustment system related to the present embodiment configured in this way will be explained below by referring to FIGS. 5 to 7.

(1) Light Intensity Adjustment Operation

First, the standard value of brightness of the target area image is set up. Here, this is a fixed value. Next, in the state without the work piece, or in the state of a work piece with no defects, etc. installed, the light irradiation device 1, the light intensity control unit 3, and the photographic device 2 are operated.

Figure 5:
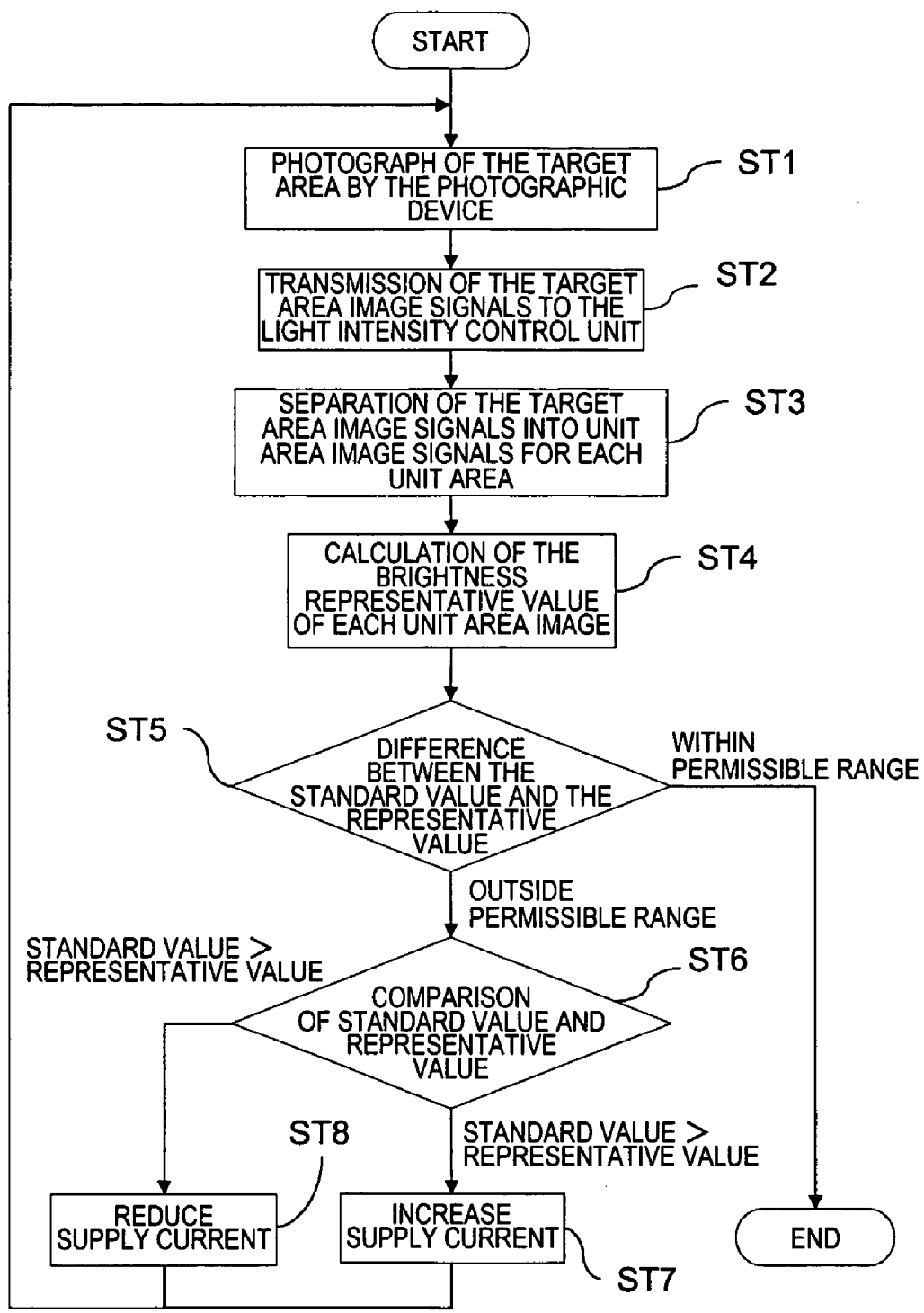
FIG. 5 is a flow chart indicating the operation of a light intensity control unit of the same embodiment.

Then, the photographic device 2 first photographs the target area A (FIG. 5 step ST1), and the target area image is transmitted to the light intensity control unit 3 as image signals (FIG. 5 step ST2).

Figure 6:
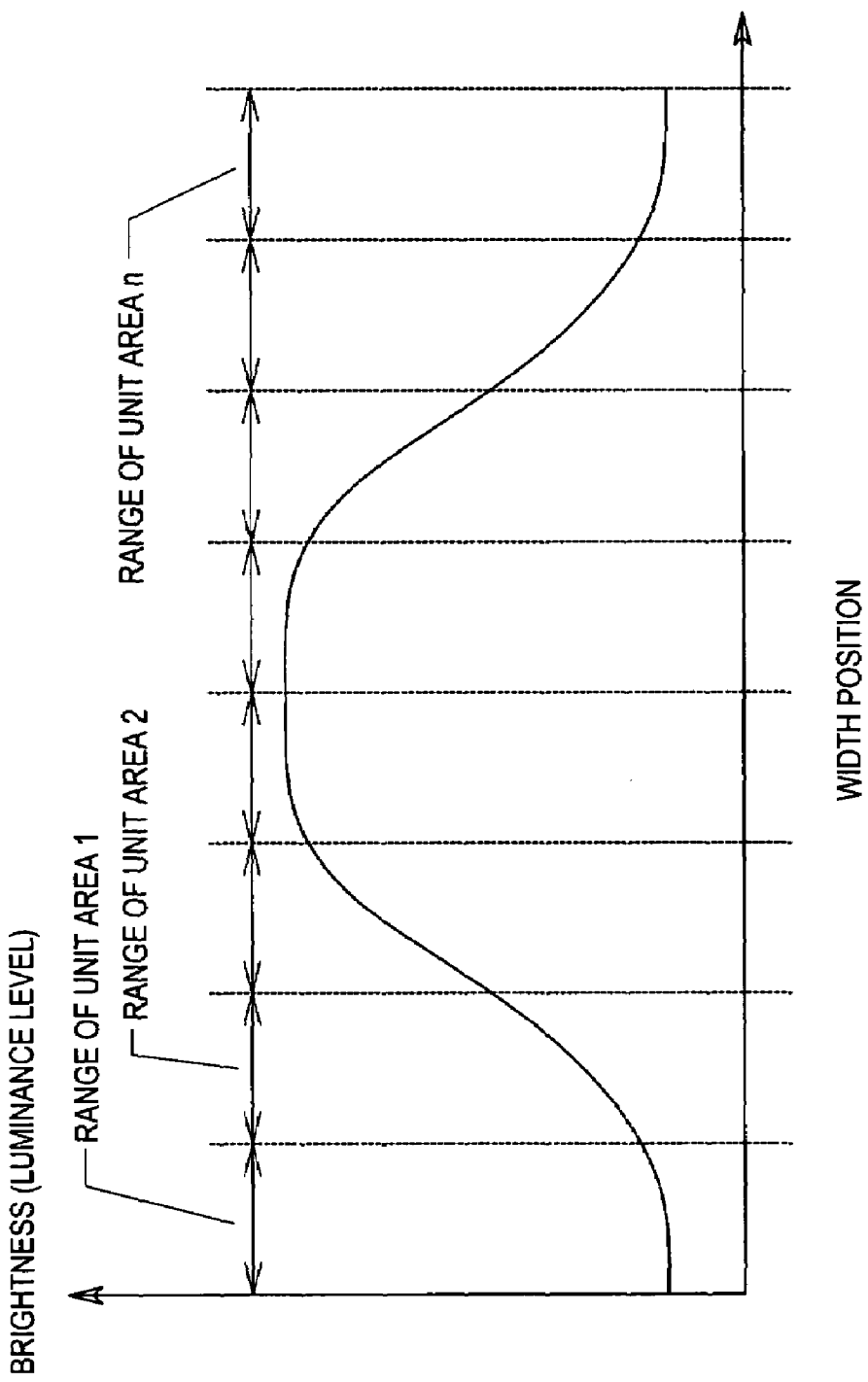
FIG. 6 is a signal diagram indicating the image signals prior to light intensity compensation in the same embodiment.
Figure 7:
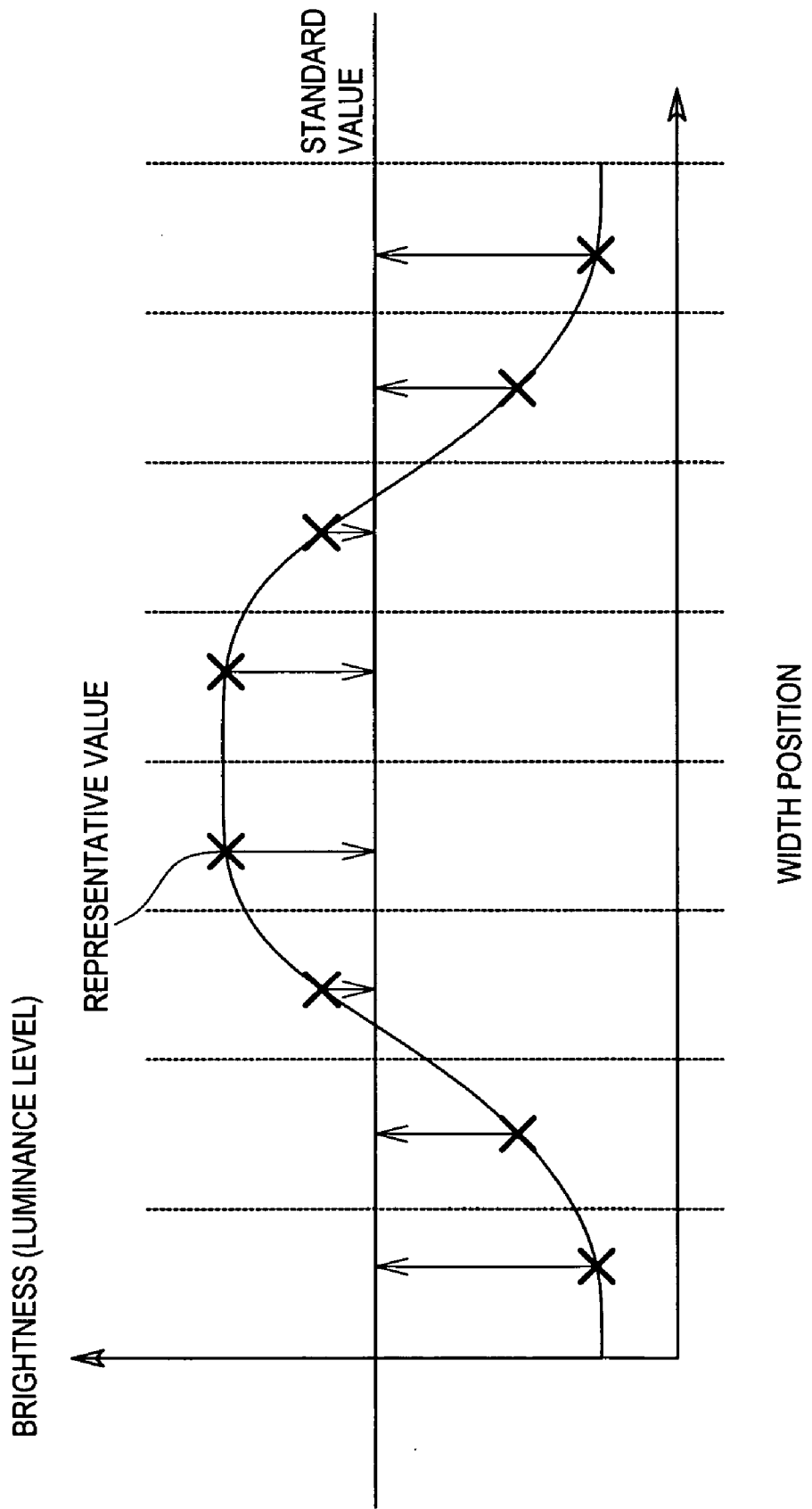
FIG. 7 is a signal diagram indicating the light intensity compensation target of the same embodiment.

At the light intensity control unit 3, as indicated in FIG. 6 and FIG. 7, said image signals are divided into the unit area image signals of each unit area UA (FIG. 5 step ST3), and the representative value of the brightness (luminance level) of the various unit area images is calculated from these signals (FIG. 5 step ST4). Then, the predetermined standard value of brightness and the representative value of said unit area images are compared, the supply currents to the corresponding power LEDs 5 are controlled based on these comparison results such that the various representative values approach said standard value (FIG. 5 steps ST6 to ST8). An FB loop is formed in this way, and the light intensity of the light irradiation device 1 is adjusted until finally the brightness of the various units of the target area image are within the permissible range in relation to the standard value (FIG. 5 step ST5).

(2) Operation of Scan Illumination

In the present embodiment, after adjusting the light intensity of the light irradiation device 1 in this way, specifically, after teaching is completed, the light intensity of the light irradiation device 1 is fixed, and scanning of the surface of the work piece will be conducted at that light intensity.

Consequently, according to the present embodiment, diminishing scan precision caused by image deterioration, etc. when compensating can be prevented because image compensation such as shading compensation, etc. by the image processor side is greatly reduced or made unnecessary. In addition, shortening scan time and improving the scan precision can be broadly promoted because the image processor can concentrate on the image processing necessary for the original scan.

Moreover, said target area A is divided into multiple unit areas UA, a 1 to 1 correspondence is set up between the various unit areas UA and the light irradiation units 11, and the light of the light irradiation units 11 mainly irradiate the corresponding unit areas UA. Therefore, when controlling the light intensity, it is clear which light irradiation unit 11 should be controlled, and the control method may be simplified.

Second Embodiment

Next, a second embodiment of the present invention will be explained based on the diagrams. Further, in the following explanation the same codes will be used for members that correspond to those of said first embodiment.

The light irradiation system of this second embodiment has nearly the same configuration as that of said first embodiment. However, there is a slight difference in the configuration of the functions of the light intensity control unit 3. The explanation below will concentrate on the points of difference from the first embodiment, and an explanation of common points will be omitted.

Figure 8:
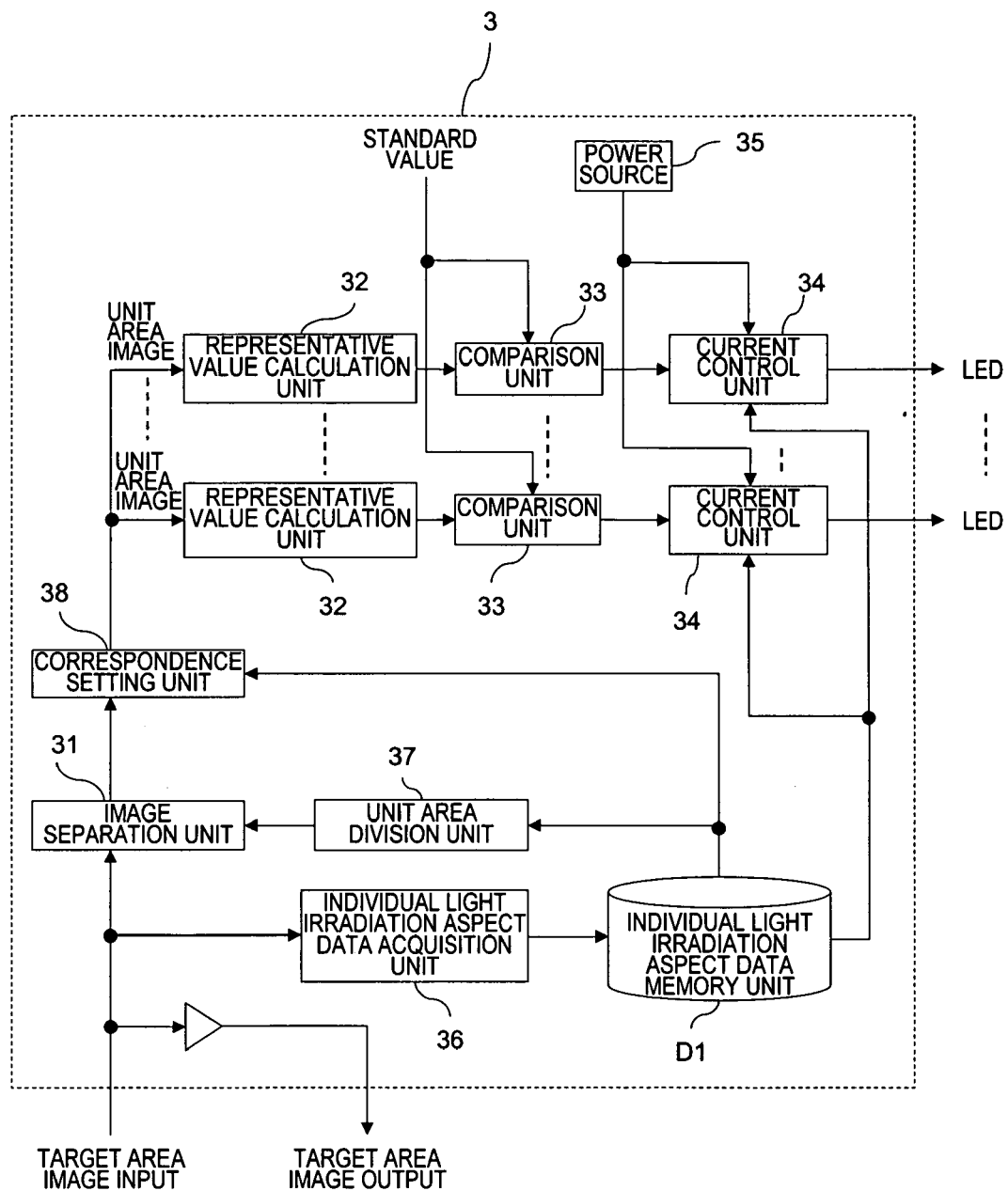
FIG. 8 is a functional block diagram of a light intensity control unit of a second embodiment of the present invention.

The light intensity control unit 3 of this embodiment is connected to the various power LEDs 5 through current cable CA, and controls the current supplied to these. As indicated in the functional block diagram in FIG. 8, comprises: a power source 35; an image separation unit 31 that separates said image signals into unit area image signals for every unit area UA; representative value calculation units 32 that calculate from these signals the representative value of the brightness (luminance level) of the various unit area images; comparison units 33 that compare the representative values of the various unit area images with a predetermined standard value of brightness; and current control units 34 that are unit light intensity control unit to control the supply current to the corresponding power LEDs 5 such that the various representative values approach said standard value based on the results of comparisons by said comparison units 33. These units are the same as in embodiment 1.

Accordingly, in addition to said configurational elements, the light intensity control unit 3 of this second embodiment further comprises: an individual light irradiation aspect data acquisition unit 36 that acquires in advance light irradiation aspects on said target area A based on the light irradiation from the individual light irradiation units 11 as individual light irradiation aspect data from said target area images; unit area division unit 37 that divides said target area A into multiple unit areas UA based on the range of light irradiation by the various light irradiation units 11 that said individual light irradiation aspect data indicates; and a correspondence setting unit 38 that sets a correspondence between each unit area UA and the one light irradiation unit 11 that mainly irradiates that area, and that light irradiation unit 11 is taken as the main light irradiation unit 11 of the unit area UA in question.

Combined with a detailed explanation of each of said parts, an example of operating the light intensity adjustment system configured in this way will be explained below.

(1) Initial Adjustment Operation

Figure 14:
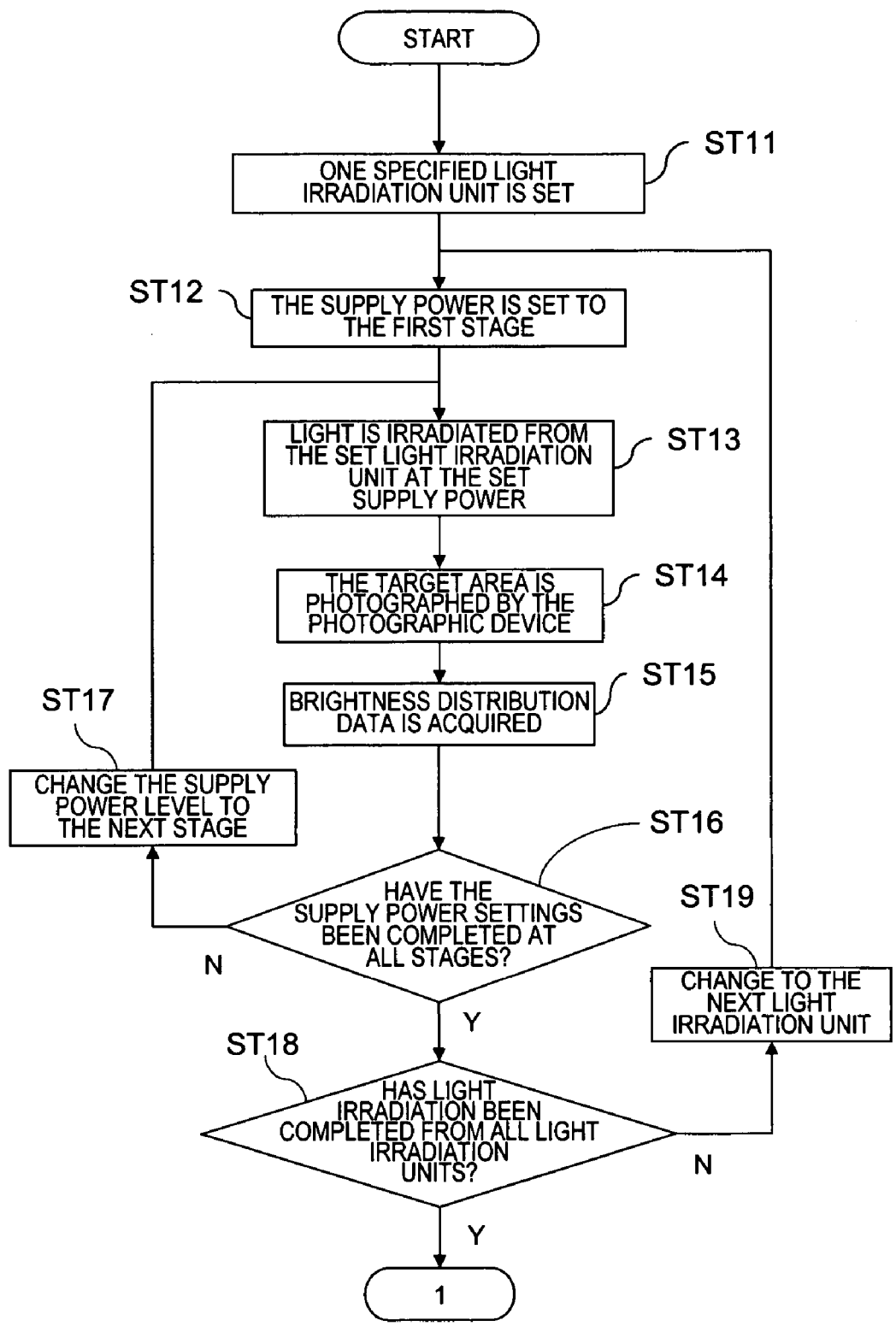
FIG. 14 is a flowchart indicating the operation of the light intensity control unit of the same embodiment.

First, the individual light irradiation aspect data acquisition unit 36 acquires in advance the light irradiation aspect on said target area A from said target area image as individual light irradiation aspect data based on the light irradiation from the light irradiation units 11 (FIG. 14 steps ST11 to ST19).

Figure 9:
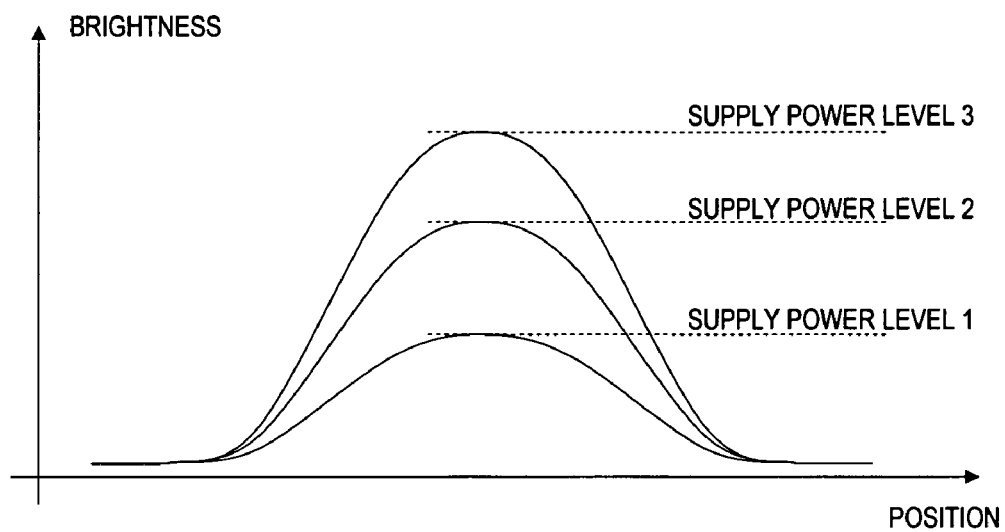
FIG. 9 is a data distribution chart graphically indicating the brightness distribution data of the same embodiment.

Concretely, light is first irradiated from one suitably set light irradiation unit 1. The supply power level is in multiple stages, and here for example, it is in three stages. Then, every time a light irradiation unit 11 is lit at each stage, the target area A is photographed by the photographic device 2, and the brightness distribution data (indicated by the graph in FIG. 9) on the target area A for each of said supply power levels is incorporated from that image data. The incorporated brightness distribution data includes a correlation between position data and brightness data, and is memorized in a predetermined region of memory. This is conducted for all light irradiation units 11 in order.

Figure 10:
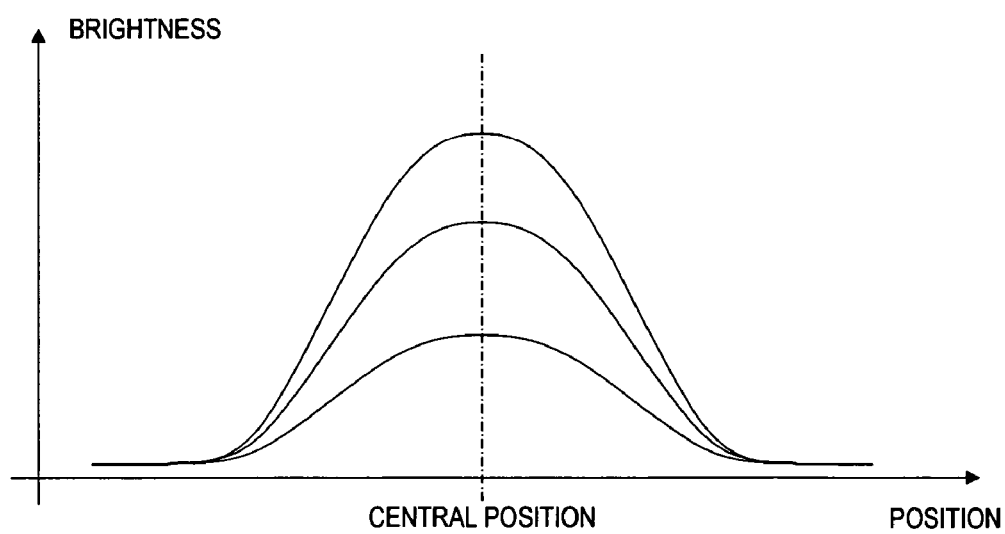
FIG. 10 is an explanatory diagram indicating a graph to explain the process of setting the central position of the light irradiation unit of the same embodiment.
Figure 11:
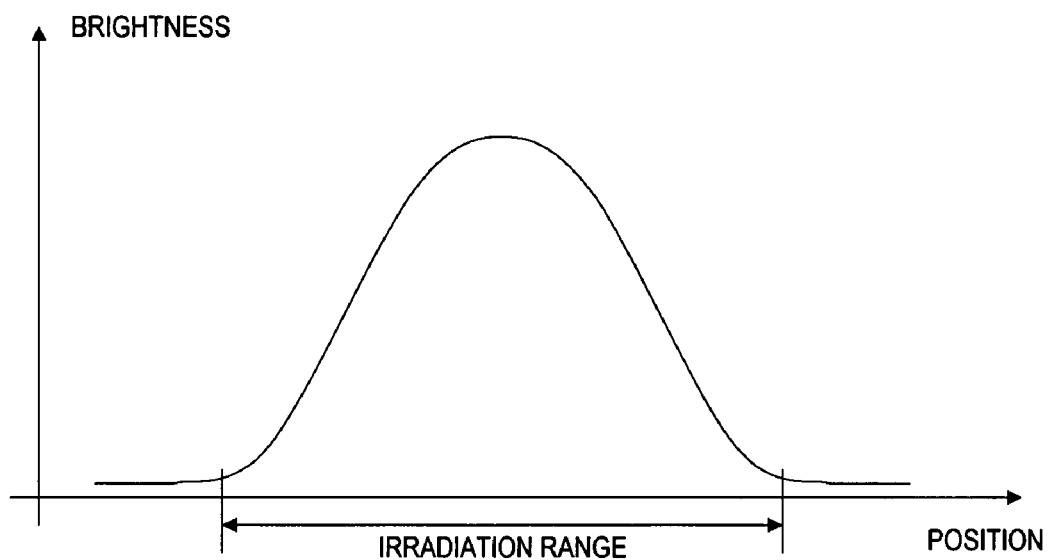
FIG. 11 is an explanatory diagram indicating a graph to explain the process of setting the irradiation range of the light irradiation unit of the same embodiment.
Figure 15:
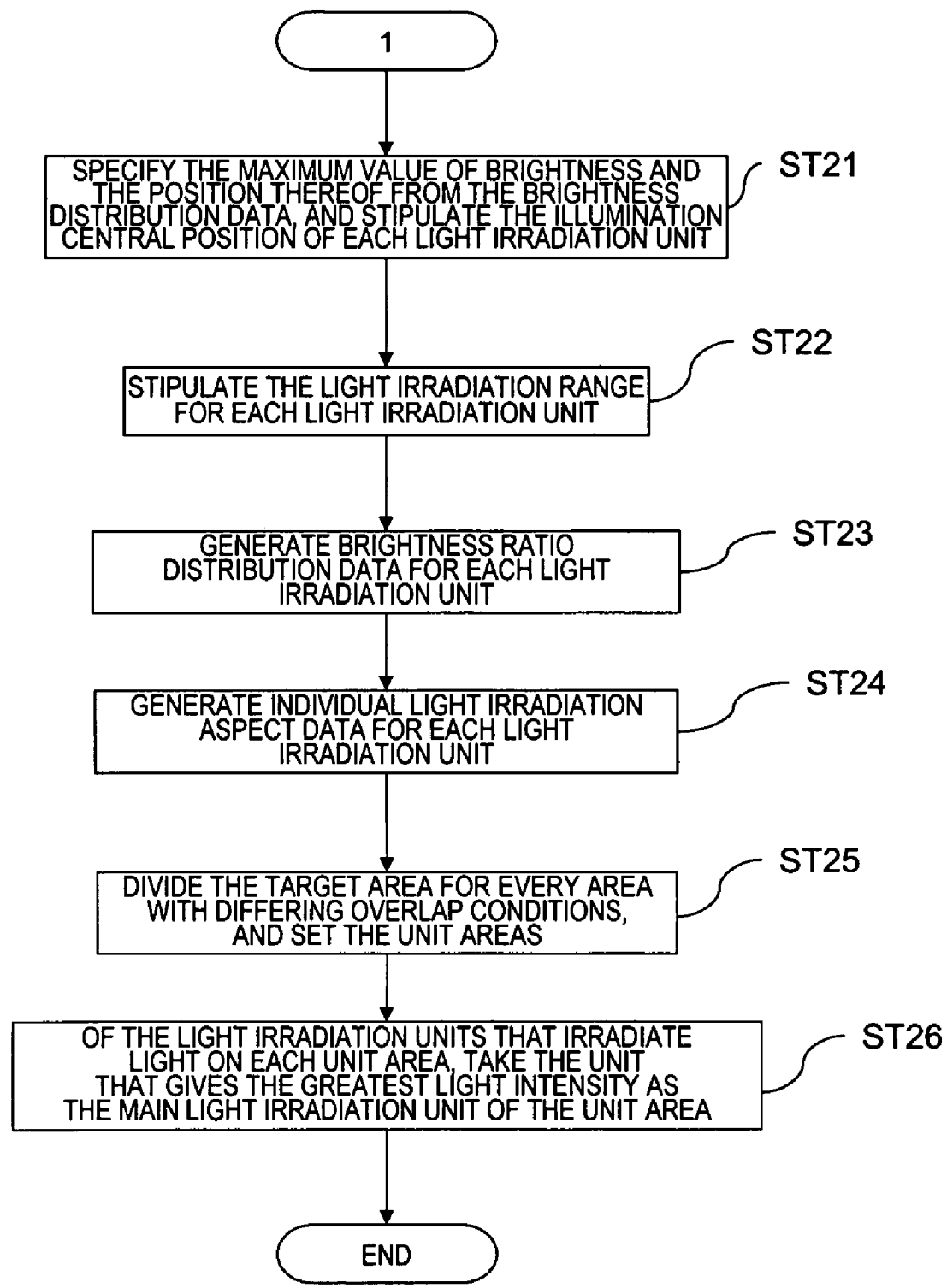
FIG. 15 is a flowchart indicating the operation of the light intensity control unit of the same embodiment.

Next, as indicated by the graph in FIG. 10, the maximum value of the brightness and that position are specified from said brightness distribution data, and this is taken as the illumination central position of the light irradiation unit 11 in question (FIG. 15 step ST21). Moreover, as indicated by the graph in FIG. 1, the bright part is specified by a predetermined brightness, and that range is taken to be the irradiation range of the light irradiation unit 11 in question (FIG. 15 step ST22).

Figure 12:
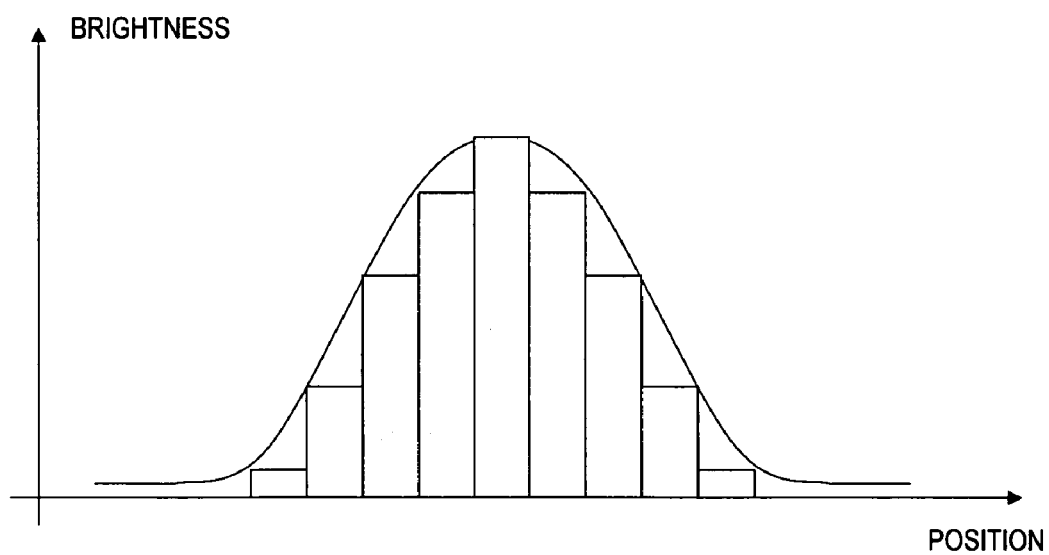
FIG. 12 is a data distribution chart using a bar graph to indicate the brightness specific distribution data of the same embodiment.

Meanwhile, if, for example, said maximum brightness value is set at 100, then brightness ratio distribution data indicating the distribution of the brightness ratio to that is produced at every power level from said brightness distribution data (FIG. 15 step ST23). The brightness ratio distribution data is indicated in FIG. 12 using a bar graph. Then, said individual light illumination aspect data including the brightness data in which the position and supply power are taken as parameters is produced as the kind of table indicated in FIG. 16 by using, for example, the least squares method to do the calculations (FIG. 15 step ST 24). As indicated in said FIG. 16, this individual light irradiation aspect data is correlated with a light irradiation unit identifier for identifying each light irradiation unit 11, and is memorized and stored in an individual light irradiation aspect data memory unit D1 set up in memory.

Next, the unit area division unit 37 divides said target area A into multiple unit areas UA.

Figure 13:
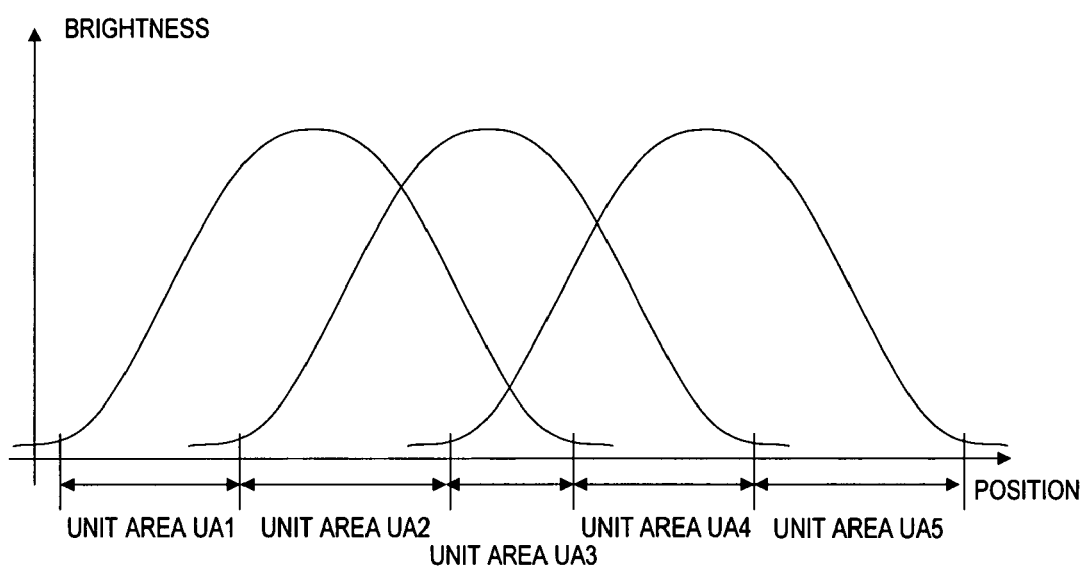
FIG. 13 is a pattern diagram indicating the method to set the unit areas of the same embodiment.

Concretely, as indicated schematically in FIG. 13, based on said individual light irradiation aspect data, the unit areas UA are set up by dividing said target area A so that the number or type of light irradiation unit 11 irradiating light on each unit area UA differs respectively, specifically, by dividing said target area A into every area where the overlap conditions differ (FIG. 15 step ST25).

Thereafter, the correspondence setting unit 38 sets up the corresponding main light irradiation unit 11 for each unit area UA. Concretely, of the light irradiation units 11 that irradiate light on a unit area UA, the one that provides the most light intensity is selected based on said individual light irradiation aspect data, and this is taken to be the main light irradiation unit 11 corresponding to the unit area UA in question (FIG. 15 step ST 26).

(2) Light Intensity Adjustment Operation

The light intensity adjustment operation is nearly the same as that of said first embodiment, and therefore a flowchart and part of the explanation will be omitted.

First, the photographic device 2 photographs the target area A, and that target area image is sent to the light intensity control unit 3 as image signals.

Meanwhile, based on the division results by said unit area division unit 37, the image separation unit 31 separates said image signals into unit area image signals for every unit area UA.

Next, the representative value calculation unit 32 calculates the representative value of the brightness (luminance level) of every unit area image from these signals.

Thereafter, the comparison unit 33 compares the predetermined standard value of brightness (in this embodiment, the entire target area A is set to the same standard value) and said representative values of the unit area images.

Then, based on these comparison results, the current control unit 34 controls the current supplied to the corresponding main light irradiation unit 11 so that the representative values approach said standard value. More concretely, taking said individual light irradiation aspect data as the parameters, the current control unit 34 outputs specifically by calculating the supply current from the brightness at said central position obtained from this data such that the difference between the representative value and the standard value enters within the permissible range.

This current control, for example, may be conducted all at once one time only, but when calculating the supply current, because this considers only the change in brightness by the main light irradiation unit 11, and does not consider the effect of the adjacent light irradiation units 11 that overlap, there is the risk that the results of calculating the difference between the representative values and the standard value will not be in the permissible range. In this case, these steps may be repeated until entering the permissible range.

(3) Scan Illumination Operation

After adjusting the light intensity of the light irradiation device 1 in this way, specifically, after completing teaching, the light intensity of the light irradiation device 1 is fixed, and the surface scan of the work piece is conducted with that light intensity.

In this way, according to the present embodiment, even if slight differences are produced in the various light intensities and irradiation angles based on fluctuations of the product quality or assembly errors in the light irradiation units 11, because the individual light irradiation aspects of the various light irradiation units 11 on the target regions are pre-measured prior to controlling the light intensity, and the various light irradiation units 11 are controlled by calculations corresponding to the individual light irradiation aspects, not only is precise control possible, it is not necessary to conduct control repeatedly until converging as with FB control, and it is also possible to speed up the process.

Other Embodiments

Further, the present invention is not limited to the embodiment above, and a variety of forms is possible. In the explanation below, the same codes are given to members corresponding to the previously described embodiments.

Figure 17:
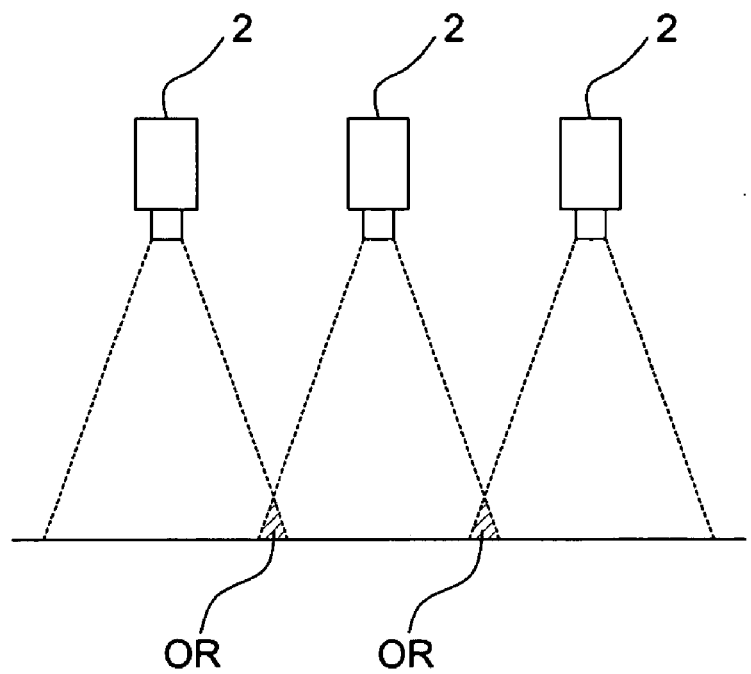
FIG. 17 is a pattern diagram indicating a photographic device of another embodiment of the present invention.

For example, as indicated in FIG. 17, if multiple photographic devices 2 are used to separate and photograph a target area A having a broad range, adjacent photographic devices 2 may take photographs that duplicate one part of said target region A. In this case, there is the problem of which image from which photographic device 2 will be the basis for light intensity control in the overlapping area. In this case, a priority ranking is given in advance to the photographic devices 2. It is preferable that for the overlapping target region A, the light intensity of said corresponding light irradiation unit 11 is controlled based on the image obtained from the photographic device 2 with the higher priority ranking, and for the target region A that the photographic device 2 with the lower priority ranking photographs, the light intensity of the light irradiation unit 11 corresponding to the other area is controlled taking the image of the previously described overlapping area as a standard.

Concretely, an explanation will be given by referring to FIG. 18 and FIG. 19.

Figure 18:
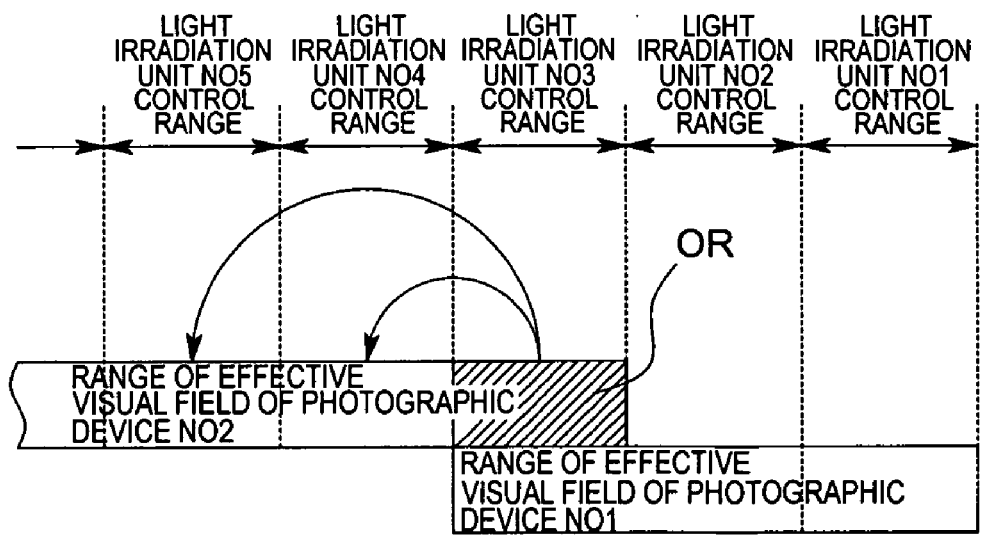
FIG. 18 is a control explanatory diagram for explaining the light intensity control of the same embodiment.

FIG. 18 indicates the case when the highest priority ranking is granted to the photographic device 2 positioned furthest to the end. In this case, first the light intensity control unit 3 controls the light intensities of the corresponding light irradiation units 11 (concretely, light irradiation unit NO1, light irradiation unit NO2, and light irradiation unit NO3 in the diagram) based on the image obtained by the photographic device 2 in question. As a result, because the light irradiation unit NO3 corresponding to the overlapping part is also controlled, that light intensity is established. Next, the light intensity control unit 3 controls the light intensities of the corresponding light irradiation units 11 (concretely, light irradiation unit NO3, light irradiation unit NO4, and light irradiation unit NO5 in the diagram) based on the image obtained by the adjacent photographic device with the second highest priority ranking. At this time, because the light intensity of the light irradiation unit NO3 has already been established, this is not controlled, the image corresponding to the light irradiation unit NO3 is taken as the standard, and the light intensities of the light irradiation units 11 corresponding to the other areas (concretely, light irradiation unit NO4, and light irradiation unit NO5 in the diagram) are controlled. If there is another adjacent photographic device 2, that photographic device 2 has the next highest priority ranking, and the successive light irradiation units 11 are controlled by the same procedure.

Figure 19:
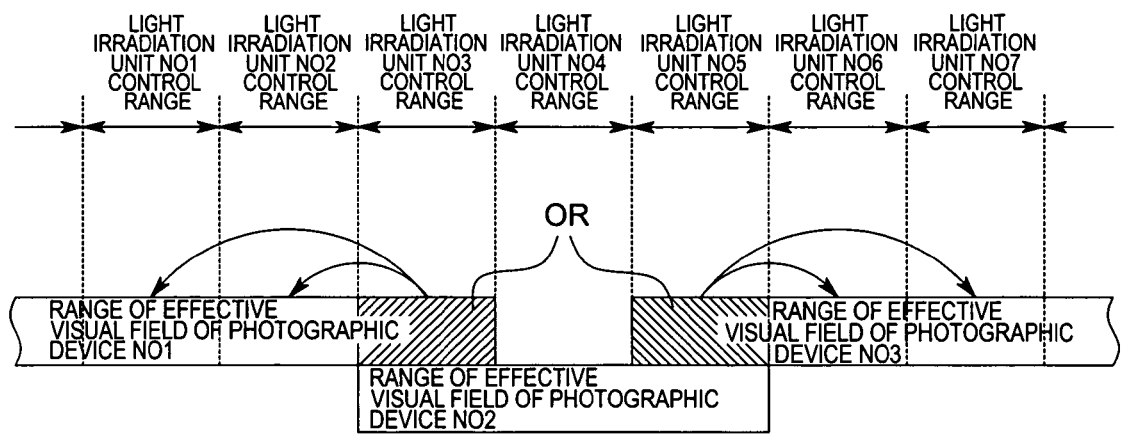
FIG. 19 is a control explanatory diagram for explaining another light intensity control of the same embodiment.

FIG. 19 indicates when the highest priority ranking is granted to the photographic device 2 positioned in the center. In this case as well, first the light intensity control unit 3 controls the light intensities of the corresponding light irradiation units 11 (concretely, light irradiation units NO3, NO4, and NO5 in the diagram) based on the image obtained by the photographic device 2 in question. As a result, because the light irradiation units NO3 and NO5 corresponding to the overlapping part are also controlled, those light intensities are established. Next, the light intensity control unit 3 controls the light intensities of the corresponding light irradiation units 11 (concretely, light irradiation units NO1, NO2, NO3, NO5, NO6, and NO7 in the diagram) based on the images obtained by both of the adjacent photographic devices 2 with the second highest priority ranking. At this time, because the light intensities of the light irradiation units NO3 and NO5 have already been established, these are not controlled, the images corresponding to those light irradiation units NO3 and NO5 are taken as the standard, and the light intensities of the light irradiation units 11 corresponding to the other areas (concretely, light irradiation units NO1, NO2, NO6, and NO7 in the diagram) are controlled. If there is another adjacent photographic device 2, that photographic device 2 has the next highest priority ranking, and the successive light irradiation units 11 are controlled by the same procedure.

That is, if a photographic device 2 is set up with the highest priority ranking, then the priority rankings are set up in the order from the adjacent device, and the light intensity control is successively conducted in that order.

Consequently, when set up in this way, in addition to being able to establish control of the light irradiation units 11 in regard to overlapping areas, a mutually unified brightness image can be obtained all at one time from the various photographic devices 2.

Meanwhile, if the images obtained by the various photographic devices do not need to be respectively unified, the corresponding light irradiation units are respectively controlled independently based on the images obtained by the various photographic devices, and for the overlapping parts, the light intensity is controlled based only on the images by whichever photographic device is predetermined, and the overlapping part of the images obtained by the other photographic device may be ignored.

Moreover, the light irradiation device may be provided with a light intensity unevenness-mitigating member that mitigates light intensity unevenness dependent on gaps between adjacent light irradiation units. If, for example, a linear shaped light irradiation device is used, it is preferable that this light intensity unevenness-mitigating member may be a lenticular lens having multiple concave grooves or convex ribs extending orthogonally to the direction of the line.

Figure 20:
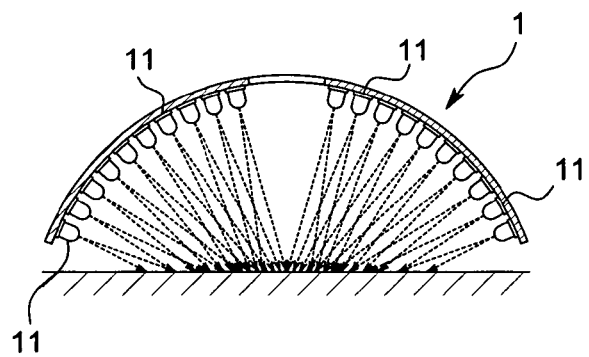
FIG. 20 is a pattern diagram indicating a light irradiation device of another embodiment of the present invention.
Figure 21:
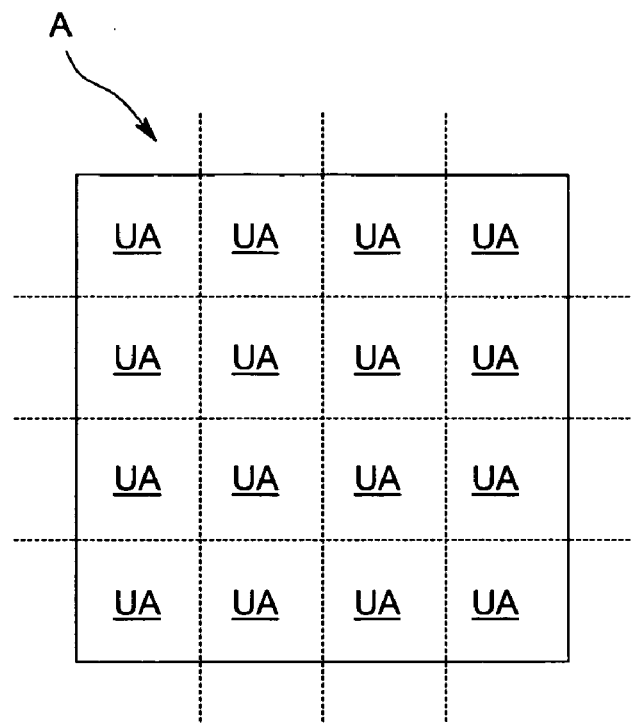
FIG. 21 is a target area diagram indicating the form of dividing the target area in another embodiment of the present invention.
Figure 22:
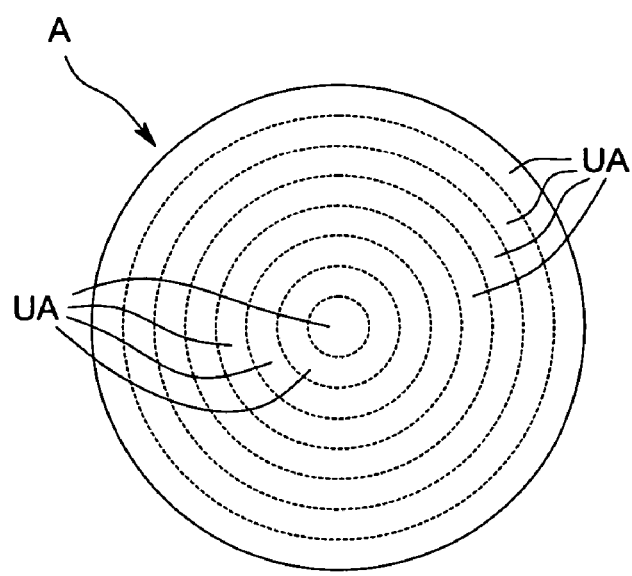
FIG. 22 is a target area diagram indicating the form of dividing the target area in another embodiment of the present invention.

If the work piece is BATCH, etc., the present invention may be used on an area photographic device having light receiving elements such as CCDs, etc. arranged in a surface shape. In this case, a light irradiation device (not indicated in the diagram) provided with multiple light irradiation units lined up in a planar shape, or a light irradiation device 1 like that indicated in FIG. 20 provided with multiple light irradiation units 11 lined up in a partial concave spherical surface may be used. The target area A may be divided into unit areas UA like the divisions of the dotted lines in FIG. 21, for example, for the former, or in FIG. 22, for example, for the latter. Further, a light diffuse plate, for example, may be cited as the light intensity unevenness-mitigating member used in this case.

Of course, the present invention can be used in the same way even with work pieces that are not translucent and scanning with reflected illumination is utilized. There is no problem even if the light irradiation device irradiates light by direct LEDs without passing through optical fibers.

Moreover, a more detailed light intensity control may be conducted by taking LEDs or the light exit ends of optical fibers as the light irradiation units respectively.

Further, the arrangement of the various parts that configure the light intensity control unit may be freely modified, and these do not have to be unified. For example, the power source and the current control unit of the light intensity control unit may be provided on the light irradiation device side, and signal cables may transmit the comparison results signals from said comparison unit to the current control unit. If this is done, it is not necessary to use many thick power cables, and the device can be made lighter. Of course, the various parts of this light intensity control unit may be configured using digital or analog circuits, and a computer and software may be used.

In addition, only the initial teaching regarding light intensity control was controlled in said embodiments, but, for example, control may be conducted intermittently, or light intensity control may be constantly and continually conducted during the scan. If this is done, immediate responses to changes in the work piece or to modification of machine types can be made, deterioration of illumination can be offset, and stable illumination is possible.

Further, when other light irradiation units other than the corresponding light irradiation unit have an effect on the brightness of the unit area image, that effect may be taken into consideration and the other light irradiation units may be controlled for additional brightness control of the unit area images. In this case, it is preferable to light the light irradiation units one at a time in advance, and to measure the light irradiation effect on the other unit areas.

Figure 23:
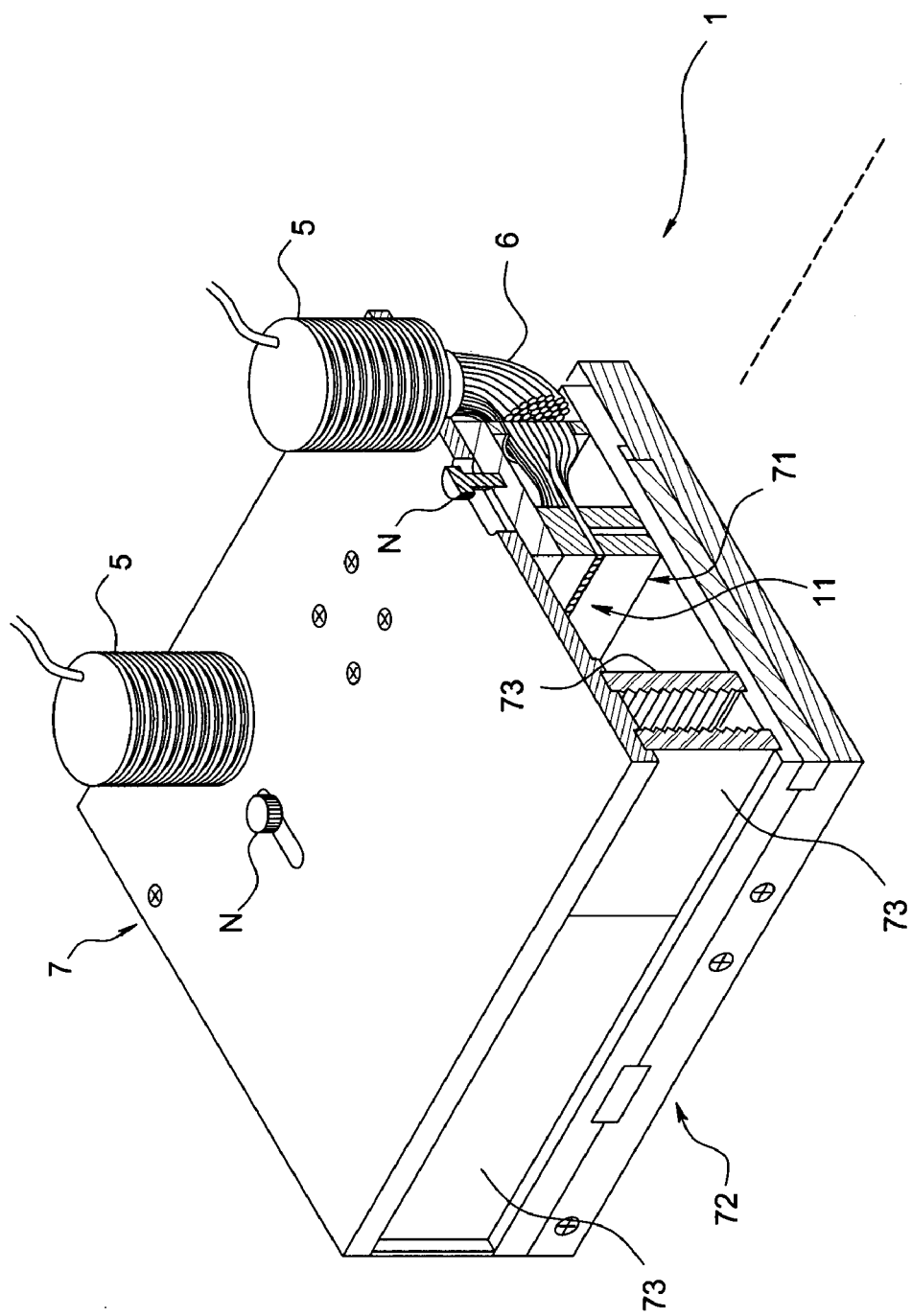
FIG. 23 is a partial cut-away perspective view diagram of a light irradiation device of another embodiment of the present invention.
Figure 24:
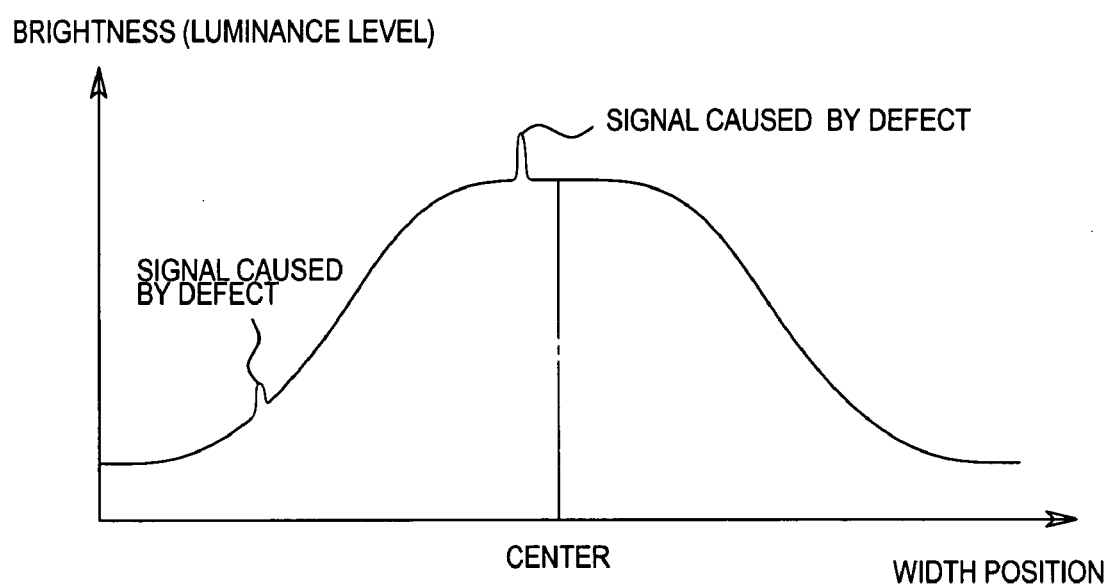
FIG. 24 is a signal diagram indicating a conventional image signal.
Figure 25:
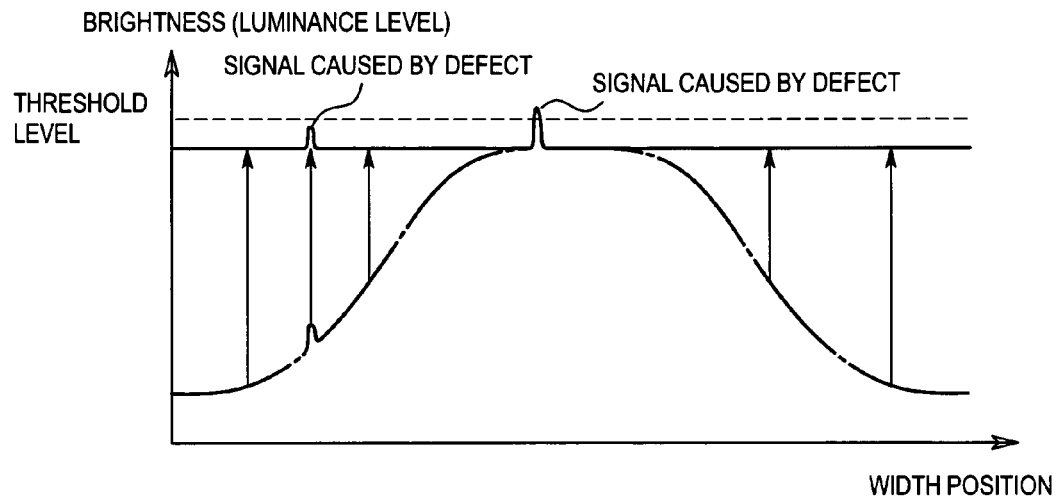
FIG. 25 is a signal diagram when adding image processing to a conventional image signal.
Figure 26:
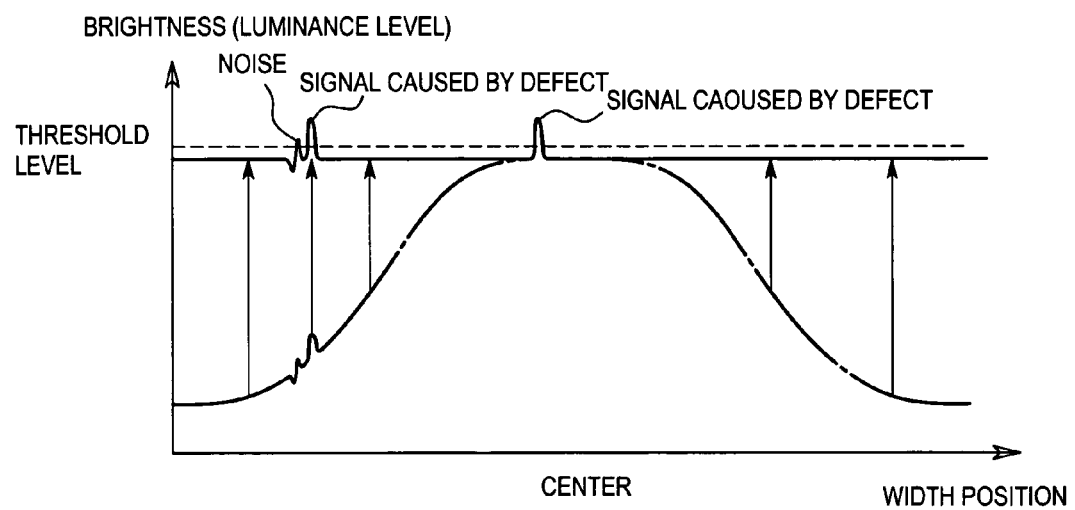
FIG. 26 is a signal diagram when adding image processing to a conventional image signal.

Moreover, as indicated in FIG. 23, the LEDs 5 of the light irradiation device 1 may be directly installed in the casing 7, the optical fibers 6 may be arranged inside of the casing. If this is done, it is not necessary to run heavy fiber bundles comprising multiple optical fibers to the outside, therefore contributing to making the device lightweight and to improving ease of use. Further, in the same diagram, the boundary wall of each irradiation unit 11 may be eliminated to make a configuration that can obtain more uniform light.

The fewer the overlapping parts of the light irradiation range there are based on the light irradiation units, the easier to control, but on the other hand, by providing light irradiation units lined up at an extremely narrow pitch, it is possible to control the distribution of brightness in an extremely smooth manner, for example, to heighten the uniformity of the brightness distribution by making many overlapping parts.

Further, in the second embodiment, brightness data included in the individual light irradiation aspect data was memorized in tables that made the position, supply power, and light irradiation unit identifier the parameters, but, for example, only the brightness data of the central position may be memorized by taking the supply power and light irradiation unit identifier as parameters, and when controlling the light intensity, the brightness data of the places separated from the central position may be taken as proportional to the brightness distribution data, and calculated every time.

In addition, the present invention is not limited to the examples indicated in the diagrams above, and may be modified in a variety of ways within the range that does not deviate from that intent.

INDUSTRIAL APPLICABILITY

As described in detail above, according to the present invention, image compensation such as shading compensation, etc. by the image processor side is greatly reduced or made unnecessary, and therefore diminishing scan precision caused by image deterioration, etc. when compensating can be prevented. In addition, shortening scan time and improving the scan precision can be broadly promoted because the image processor can concentrate on the image processing necessary for the original scan.

The invention claimed is:

1. A light intensity adjustment system comprising:
   a light irradiation device that irradiates light on a predetermined target area set up on a work piece;
   a photographic device that photographs the target area and outputs obtained target area images to an image processor for the purpose of a surface scan, wherein said light irradiation device has multiple light irradiation units that are independently light intensity adjustable, and the light intensity adjustment system further comprises a light intensity control unit that controls respective light intensities of said light irradiation units so that brightness of the various parts of the target area images output by said photographic device approaches a predetermined standard value; and
   an individual light irradiation aspect data acquisition unit, whereby light irradiation aspects on said target area based on the light irradiated from the individual light irradiation units are acquired in advance from said target area images and are memorized in a predetermined memory region as individual light irradiation aspect data, and said light intensity control unit controls the light intensities of said light irradiation units based on said individual light irradiation aspect data.

2. The light intensity adjustment system according to claim 1, wherein said light intensity control unit controls the light intensities of the various light irradiation units to make the brightness of the various parts of said target area image uniform.

3. The light intensity adjustment system according to claim 1, wherein said individual light irradiation aspect data at least indicates a light irradiation range and brightness distribution on the target area based on the various light irradiation units supplied a predetermined power.

4. The light intensity adjustment system according to claim 1, configured so that said target area is divided into multiple unit areas, each unit area corresponds to one light irradiation unit that mainly irradiate the unit area, and the light irradiation unit is taken as the main light irradiation unit of the unit area.

5. The light intensity adjustment system according to claim 4 configured so that said unit areas and the light irradiation units are given a one to one correspondence.

6. The light intensity adjustment system according to claim 4, wherein, based on the light irradiation range of each light irradiation unit that said individual light irradiation aspect data indicates, said target area is divided into multiple unit areas so that the number or type of light irradiation unit that irradiates light on the various unit areas differ respectively.

7. The light intensity adjustment system according to claim 6, wherein, based on the brightness distribution of each light irradiation unit that said individual light irradiation aspect data indicates, for each unit area, the light irradiation unit that gives the greatest light intensity is taken as the main light irradiation unit of the unit area.

8. The light intensity adjustment system according to claim 4, wherein said light intensity control unit comprises an image separation unit that separates said target area image into images of said various unit areas, a representative value calculation unit that calculates a representative value of the brightness of the various unit area images, a comparison unit that compares a predetermined standard value of the brightness and the representative value of said each unit area image, and a unit light intensity control unit that controls the light intensity of the main light irradiation unit corresponding to the unit area so that each representative value approaches said standard value based on comparison results by said comparison unit.

9. The light intensity adjustment system according to claim 8, wherein said representative value calculation unit calculates the mean brightness of the unit area image and takes the value as the representative value.

10. The light intensity adjustment system according to claim 1, wherein the light irradiation device comprises light irradiation units lined up in a linear or surface shape.

11. The light intensity adjustment system according to claim 10, wherein the light irradiation device comprises a light intensity unevenness-mitigating member that mitigates unevenness of light intensity dependent on gaps between adjacent light irradiation units.

12. The light intensity adjustment system according to claim 1, comprising multiple photographic devices, wherein the photographic devices photograph by separating said target area, and if either adjacent photographic device photographs by duplicating a part of said target area, for the overlapping target area, the light intensity of the corresponding light irradiation unit is controlled based on the image obtained by the photographic device with the higher priority ranking, and for the target region that the photographic device with a lower priority ranking photographs, the light intensity of the light irradiation unit corresponding to that other area is controlled taking said image of the overlapping target area as the standard.

13. A light intensity adjustment system comprising:
   a light irradiation device that has multiple light irradiation units that are independently light intensity adjustable and that irradiates light toward predetermined target areas;
   a photographic device that photographs said target areas through a lens and outputs target area images as being photographed images;
   a light intensity control unit that controls the respective light intensities of said light irradiation units so that the brightness of each part of the target area images that said photographic device has output approaches a predetermined standard value; and
   an individual light irradiation aspect data acquisition unit, whereby light irradiation aspects on said target area based on the light irradiated from the individual light irradiation units are acquired in advance from said target area images and are memorized in a predetermined memory region as individual light irradiation aspect data, and said light intensity control unit controls the light intensities of said light irradiation units based on said individual light irradiation aspect data.

14. A light intensity adjustment system comprising:
   a light irradiation device that irradiates light on a predetermined target area set up on a work piece; and a photographic device that photographs the target area and outputs obtained target area images to an image processor for the purpose of a surface scan, wherein said light irradiation device has multiple light irradiation units that are independently light intensity adjustable, and the light intensity adjustment system further comprises a light intensity control unit that controls respective light intensities of said light irradiation units so that brightness of the various parts of the target area images output by said photographic device approaches a predetermined standard value, wherein the light irradiation device comprises a light intensity unevenness-mitigating member that mitigates unevenness of light intensity dependent on gaps between adjacent light irradiation units.

* * * * *

UNITED STATES PATENT AND TRADEMARK OFFICE
CERTIFICATE OF CORRECTION

| | | |
|---|---|---|
| PATENT NO. | : 7,643,746 B2 | Page 1 of 1 |
| APPLICATION NO. | : 10/534613 | |
| DATED | : January 5, 2010 | |
| INVENTOR(S) | : Yoneda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1271 days.

Signed and Sealed this

Sixteenth Day of November, 2010

David J. Kappos
*Director of the United States Patent and Trademark Office*